(12) United States Patent
Hell et al.

(10) Patent No.: US 7,764,369 B2
(45) Date of Patent: Jul. 27, 2010

(54) METHOD OF PRODUCING SPATIAL FINE STRUCTURES

(75) Inventors: Stefan Hell, Göttingen (DE); Volker Westphal, Hannover (DE); Norbert Quaas, Göttingen (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 500 days.

(21) Appl. No.: 11/856,887

(22) Filed: Sep. 18, 2007

(65) Prior Publication Data

US 2008/0018891 A1    Jan. 24, 2008

Related U.S. Application Data

(63) Continuation-in-part of application No. PCT/EP2006/002526, filed on Mar. 20, 2006.

(30) Foreign Application Priority Data

Mar. 19, 2005  (DE) .................. 10 2005 012 739

(51) Int. Cl.
*G01N 21/00* (2006.01)
*G01J 3/30* (2006.01)

(52) U.S. Cl. .................................. 356/237.5; 356/317

(58) Field of Classification Search ......... 356/317–318, 356/239.3, 237.5
See application file for complete search history.

(56) References Cited

U.S. PATENT DOCUMENTS

| | | | | |
|---|---|---|---|---|
| 5,731,588 | A * | 3/1998 | Hell et al. ............... | 250/458.1 |
| 5,777,342 | A | 7/1998 | Baer | |
| 5,965,446 | A * | 10/1999 | Ishikawa ................ | 356/237.1 |
| 7,064,824 | B2 | 6/2006 | Hell | |
| 7,253,893 | B2 | 8/2007 | Hell et al. | |

(Continued)

FOREIGN PATENT DOCUMENTS

| DE | 101 54 699 A1 | 5/2003 |
|---|---|---|
| WO | WO 95/21393 | 2/1995 |

OTHER PUBLICATIONS

Hell, Stefan W., "Toward Fluorescence Nanoscopy", Nature Biotechnology, vol. 21, No. 11, Nov. 2003, pp. 1347-1355.

*Primary Examiner*—Kara E Geisel
(74) *Attorney, Agent, or Firm*—Thomas, Kayden, Horstemeyer & Risley, LLP

(57) ABSTRACT

A method of producing spatial fine structures comprises the steps of: selecting a luminophore from the group of luminophores displaying two different states, one of the two states being an active state in which luminescence light is obtainable from the luminophore, the other of the two states being an inactive state in which no luminescence light is obtainable from the luminophore, and the luminophore being reversibly, but essentially completely, transferable out the one state into the other state by means of an optical signal; adding the luminophore to a material; forming a spatial fine structure of the material; and fluorescence-microscopically examining whether the desired fine structure is present. The step of fluorescence-microscopically examining comprises the substeps of: outside measuring points of interest, transferring the luminophore into the other state with the optical signal, the luminophore being essentially completely transferred into the inactive state outside the measuring points, and measuring luminescence light only emitted by the luminophore in the active state, to even resolve lines of the fine structure at a distance of less than 100 nm.

30 Claims, 2 Drawing Sheets

U.S. PATENT DOCUMENTS

| | | | |
|---|---|---|---|
| 2001/0045523 A1* | 11/2001 | Baer | 250/459.1 |
| 2001/0045529 A1* | 11/2001 | Iketaki et al. | 250/493.1 |
| 2002/0141052 A1* | 10/2002 | Iketaki | 359/386 |
| 2003/0036006 A1 | 2/2003 | Feke et al. | |
| 2004/0212799 A1* | 10/2004 | Hell | 356/317 |
| 2005/0111089 A1* | 5/2005 | Baer | 359/368 |
| 2006/0038993 A1 | 2/2006 | Hell | |
| 2006/0044985 A1* | 3/2006 | Hell | 369/100 |
| 2008/0070323 A1* | 3/2008 | Hess et al. | 436/514 |

* cited by examiner

METHOD OF PRODUCING SPATIAL FINE STRUCTURES

CROSS REFERENCE TO RELATED APPLICATIONS

This application is a continuation in part of International Patent Application PCT/EP2006/002526 entitled "Verfahren zur Herstellung räumlicher Feinstrukturen", filed on Mar. 20, 2006, and claiming priority to co-pending German Patent Application No. DE 10 2005 012 739.8 also entitled "Verfahren zur Herstellung räumlicher Feinstrukturen", filed Mar. 19, 2005.

FIELD OF THE INVENTION

The present invention generally relates to a method of producing spatial fine structures. Particularly, the present invention relates to a method of producing spatial fine structures comprising the steps of adding a luminophore to a material, forming a spatial fine structure of the material, and fluorescence-microscopically examining whether the desired fine structure is present. The spatial fine structures produced in this way are artificial, i.e. man-made fine structures. More particularly, the invention relates to a method in which the spatial fine structures are produced lithographically.

In the present description, the term "fine structure" particularly refers to microstructures and nanostructures, i.e. to structures with detail dimensions in the micrometer and nanometer range.

BACKGROUND OF THE INVENTION

Methods of lithographically producing spatial fine structures comprising the steps of forming a spatial fine structure of a material, and microscopically examining whether the desired fine structure is present, are used for forming conductor fine structures or insulator fine structures in the production of electronic semiconductor devices. To this end, for example, a layer of a radiation-sensitive material is applied to a semiconductor substrate. The term "radiation-sensitive" refers to the fact that the state of this material can be changed by means of radiation in such a way, for example, that it is possible to easily remove the irradiated areas of the layer with a solvent, while the not irradiated areas of the layer remain untouched by the solvent. Typically, various phenolic resins, acrylic polymers, alicyclic polymers and fluoric polymers are used as a basis for suitable radiation-sensitive materials. Any radiation-sensitive material is particularly sensitive to an electromagnetic radiation of a certain wavelength range, which may vary from the medium UV-range to the X-ray (Roentgen) range. The radiation-sensitivity of the material of the layer is, for example, based on photo-induced local conversion into an acid, or, complementary, on photo-induced local cross-linking. The term "radiation-sensitive" can, however, also refer to a sensitivity of the material to electron radiation or to other particle beams. In each case of the known method of lithographically producing spatial fine structures, the layer applied to the substrate is irradiated within defined spatial areas in order to convert the material in these spatial areas as compared to the not irradiated areas so that these areas of the material are distinguishable from each other. Subsequently, developing of the illuminated layer takes place, which—as a rule—removes the material in those spatially defined areas, in which the layer has been irradiated. In principle, however, developing can also result in that the material of the layer is removed in the not irradiated areas. In those methods known from the production of electronic semiconductor devices the presence of the desired fine structure is checked by electron microscopy. Electron microscopy is used in order to spatially dissolve the obtained fine structure to a maximum extent. The efforts to be taken for a scanning electron microscopic examination of the layer, however, are considerably high. The substrate with the respective layer must be locked into high vacuum equipment, as electron microscopy can only be operated under high vacuum. This means that no volatile substances, which could impair the high vacuum and/or damage the high vacuum equipment, may be emitted by the substrate, the layer, and any substance or article which is brought into the high vacuum equipment together with the substrate and the layer. Further, the efforts for the installation and the operation of an electron microscope are quite high.

At present, however, very few alternatives to an electron microscopic investigation are available in methods of producing lithographic fine structures, if a resolution is to be achieved within the range of better than 150 nm. State of the art circuit board tracks in microelectronics already display widths down to 90 nm with even narrower track distances. The available alternatives to electron microscopy are methods in which the fine structure to be examined is scanned with a probe. Atomic Force Microscopy (AFM) and Scanning Nearfield Optical Microscopy (SNOM) belong to those alternatives, which require no high vacuum, but which, like in the case of raster electron microscopy, require an accurate and thus laborious adjustment of the cleaned fine structure with regard to the sensible arrangement for displacing the respective probe, and which are extremely slow as compared to the size of the examined fine structure. Thus it seems to be that the efforts for microscopic investigation in the known methods of lithographically producing spatial fine structures can only be significantly reduced in that not all lithographically produced fine structures, but only a few samples of them are examined. This, however, quite substantially increases the danger of incorrectly produced electrical devices.

A method of producing spatial fine structures comprising the steps of adding a luminophore to a material, forming a spatial fine structure of the material, and fluorescence-microscopically examining whether the desired fine structure is present, luminescence light emitted by the luminophore being measured, is known from US 2003/0036006 A1. Here, a so-called photoresist is doped with a luminophore which is tuned to the photoresist in such a way that it exhibits a different fluorescence behavior, i.e. another wavelength of the fluorescence light, depending on whether it is present within an irradiated or a not irradiated area of the photoresist. The exposed photoresist is analyzed using conventional fluorescence microscopy by which a spatial resolution in the order of magnitude of the wavelength of the fluorescence light is achieved. Further, the fine structure which is generated in the photoresist by irradiation is not imaged directly in the known method; instead, it is determined along a line across the photoresist whether the fluorescence light displays a certain intensity modulation having the spatial frequency of the desired fine structure. If this intensity modulation is present, it is assumed that an illumination device for illuminating the photoresist is correctly focused. The maximum intensity modulation of less than 10%, which is, for example, registered with a fine structure of lines having a distance of 440 nm using fluorescence light having a wavelength of about 515 nm, is completely insufficient for actually imaging the fine structure, which was produced by illuminating the photoresist. Line distances of fine structures produced in state of the art semiconductor technology by means of photoresists are smaller than 100 nm and could in no way be detected by the fluorescence-microscopic method described in US 2003/0036006 A1. According to US 2003/0036006 A1 itself, an electron microscopic imaging method (SEM) is used for actually imaging the produced fine structure.

A method of fluorescence-microscopically examining a sample, which and/or an interesting structure of which has previously been stained with a fluorescence dye, is, for example, known from DE 101 54 699 A1, corresponding to U.S. Pat. No. 7,253,893 B2. In this method, which is also known as STED (Stimulated Emission Depletion) fluorescence microscopy, a fluorescence dye, with which the sample and/or the interesting structure of the sample has been stained in a previous step, is first transferred into an excited energetic state with an exciting optical signal. The usual diffraction limit of optical methods of $\lambda/(2n \sin \alpha)$ applies to the spatial resolution In this optical excitation, $\lambda$ being the wavelength of the light used, n being the refractive index of the sample, and a being the half aperture angle of the objective used. In order to get below this limit, the optically excited state of the fluorescence dye is de-excited again with a de-exciting optical signal outside a desired measuring point, in which the de-exciting optical signal displays a zero point; i.e. the fluorescence dye in the sample is forced to stimulated emission by means of the de-exciting optical signal everywhere outside the measuring point. The dimensions of the resulting still fluorescent measuring point, i.e. the spatial resolution of remaining fluorescence, can be reduced clearly below the usual optical resolution limit in that the de-exciting optical signal is applied to the sample at such an intensity outside the desired measuring point that a saturation is reached in the de-excitation by stimulated emission. Thus, the fluorescence dye in the sample is still in the excited state only in a very closely limited area around the zero point of the intensity distribution of the de-exciting optical signal. Accordingly, it can only fluoresce within this spatially limited area.

According to Hell, *Nature Biotechn.*, 21, 1347-1355, the size of the fluorescent measuring point $\Delta x$ and thus the spatial resolution in STED fluorescence microscopy follows $\Delta x = \lambda / (2n \sin \alpha \sqrt{(I/I_S)})$, $\lambda$ being the wavelength of the de-exciting optical signal, n being the refractive index of the sample, $\alpha$ being the half aperture angle of the objective used, I being the irradiation intensity of the de-exciting optical signal and $I_S$ being a saturation intensity. The saturation intensity $I_S$ is a characteristic intensity, at which, from a statistics point of view, the fluorescence dye in the sample is de-excited by 50% due to the effect of the de-exciting optical signal.

Another method of fluorescence microscopy in which the spatial resolution can fall below the diffraction limit is known as GSD (Ground State Depletion) fluorescence microscopy. Here, the fluorescence dye is not de-excited after it has initially been excited in order to transfer it into a non-fluorescent state outside the desired measurement point. Instead, the fluorescence dye outside the desired measuring point is transferred out of its ground state into a state in which it cannot be excited for fluorescence even before the excitation of the fluorescence dye takes place.

SUMMARY OF THE INVENTION

The present invention relates to a method of producing spatial fine structures comprising the steps of: selecting a luminophore from the group of luminophores displaying two different states, one of the two states being an active state in which luminescence light is obtainable from the luminophore, the other of the two states being an inactive state in which no luminescence light is obtainable from the luminophore, and the luminophore being reversibly, but essentially completely, transferable out the one state into the other state by means of an optical signal; adding the luminophore to a material; forming a spatial fine structure of the material; and fluorescence-microscopically examining whether the desired fine structure is present, the step of fluorescence-microscopically examining comprising the sub-steps of: outside measuring points of interest, transferring the luminophore into the other state with the optical signal, the luminophore being essentially completely transferred into the inactive state outside the measuring points, and measuring luminescence light only emitted by the luminophore in the active state.

Particularly, the present invention relates to a method of producing spatial fine structures comprising the steps of selecting a material from the group of radiation sensitive materials; selecting a luminophore from the group of luminophores displaying two different states, one of the two states being an active state in which luminescence light is obtainable from the luminophore, the other of the two states being an inactive state in which no luminescence light is obtainable from the luminophore, and the luminophore being reversibly, but essentially completely, transferable out the one state into the other state by means of an optical signal; adding the luminophore to the material; forming a spatial fine structure of the material, the step of forming comprises the sub-steps of: depositing a layer of the material onto a substrate, irradiating the deposited layer within spatially defined areas, and developing the irradiated layer in that parts of the layer are removed and the desired fine structure remains; and fluorescence-microscopically examining whether the desired fine structure is present, the step of fluorescence-microscopically examining by which even lines at a distance of less than 100 nm are resolved comprising the sub-steps of: outside measuring points of interest, transferring the luminophore into the other state with the optical signal, the luminophore being essentially completely transferred into the inactive state outside the measuring points, and measuring luminescence light only emitted by the luminophore in the active state, an intensity modulation of the luminescence light over a scan across the lines at a distance of less than 100 nm amounting to at least 20% of a maximum intensity of the luminescence light during the scan.

In the new method for producing spatial fine structures, a luminophore which is not directly necessary for forming the fine structure is added to the material of which the fine structure is actually formed afterwards. In the new method, however, it can only be done without adding the luminophore to the material for the fine structure, if the material already comprises such a luminophore. This, however, will not be the standard case. After forming the fine structure of the material comprising the luminophore, it can be examined by measuring luminescence light emitted by the luminophore to check whether the fine structure is present as desired.

Mainly, but not exclusively, known fluorescence dyes are suitable as the luminophore for use in the new method. The physical event responsible for the luminescence of the luminophore does indeed not matter; this event does not need to be fluorescence. If, in the following, detailed reference is made to a fluorescence dye as an example of a luminophore for use in the new method, this may not be interpreted in that the particular statements made do only apply to a fluorescence dye. Instead, the term fluorescence dye is to be interpreted as equal to the term luminophore as long as the particular context does not make clear that a particular statement only applies to a fluorescence dye. The same applies to fluorescence light as an example of luminescence light.

In the new method, luminescence light which is emitted by the luminophore is measured in the step of microscopically examining whether the desired fine structure is present. I.e. the measurement of luminescence light in the new method can also be called luminescence microscopy. In the following, it will be referred to fluorescence microscopy as a particular example of luminescence microscopy; however, also the term fluorescence microscopy or fluorescence-microscopically examining is only used as a synonym for measuring luminescence light from the luminophore with spatial resolution here, as long as nothing different is explicitly stated.

In the technical field of fluorescence microscopy, various measures are known which are suitable for increasing the spatial resolution so that the spatial resolution is sufficient for examination of artificial fine structures which are of commercial interest at present and in the foreseeable future. One could for example consider a so called confocal arrangement in a fluorescence-microscopic examination setup or a multi-photon excitation of the fluorescence dye to increase the spatial allocation of the measured or produced fluorescence light to a particular measurement point.

In the new method, however, a luminophore is used which has two states which differ from each other with regard to their luminescence properties, the luminophore being reversibly, but essentially completely transferable out of one into the other state by an optical signal. Thus, outside a spatial area, the dimensions of which fall below the usual limit of the spatial resolution in optical methods of $\lambda/(2n \sin \alpha)$ (diffraction limit), the luminophore can be transferred with the optical signal into a state in which the luminescence properties of the luminophore differ from that one within that spatial area. This allows for measuring the luminescence light from the luminophore with a spatial resolution of better than $\lambda/(2n \sin \alpha)$, $\lambda$ being the wavelength of the optical signal for transferring the luminophore from one state into the other. The term "essentially completely transferring the luminophore from its one state into its other state" is used here, if at least 80%, preferably at least 90%, more preferably at least 96% and most preferably at least 99% of the luminophore are transferred into the other state.

In measuring the luminescence light, the luminophore is particularly transferred into an inactive state in which it does not emit luminescence light outside measuring points of interest. Due to the fact that this transfer between the states of the luminophore is excited up to saturation by means of a signal only having a zero-point at the actual measuring point of interest, the spatial resolution in measuring the luminescence light is highly increased.

Particularly, the luminophore can be transferred into its inactive state by stimulated emission out of a previously excited state outside the actual measuring points of interest so that it only remains in the excited state within the measuring points of interest. Thus, detected luminescence light can only originate out of the actual measuring points of interest. The same result is achieved, however, if the luminescence dye is transferred outside the actual measuring point into a state in which it is not able to luminesce at all by means of depleting its ground state, for example.

An increased spatial resolution can also be achieved by inversely transferring the luminophore out of its inactive state into its active state everywhere outside the present measuring point of interest. Then, the relevant signal having the increased spatial resolution is the reduced or even extinct luminescence light out of the measuring points.

The luminophore can be added to the material of which the fine structure is formed at a concentration of $10^{-6}$ Mol/liter up to $10^{-2}$ Mol/liter. Preferably, it is added at a concentration of $10^{-7}$ Mol/liter up to $10^{-6}$ Mol/liter. Thus, a comparatively small amount of luminophore is sufficient, to be able to microscopically examine the produced fine structure by measuring the luminescence light. In other words, the luminophore will not affect the chemical composition of the fine structure. Those skilled in the art will be able to select a particular luminophore from the known luminophores in a suitable way.

The new method can be applied in the production of various artificial fine structures. The fine structure can be a fine structure which is still present in a final product, like for example a microelectronics product. Thus, the fine structure as such can, for example, be a conductive track. The fine structure, however, can also be a temporary structure, like for example a mask, which is afterwards used for producing a further complementary fine structure and which is then removed so that it is no longer present in the final product.

A particular and preferred application of the new method is the lithographic production of spatial fine structures. This production starts from a radiation sensitive material. For forming the fine structure, a layer of the material is deposited on a substrate, the deposited layer is irradiated in defined spatial areas, and the irradiated layer is developed, parts of the layer being removed so that the desired fine structure remains.

In the new method, the radiation sensitive material can be sensitive to UV-radiation and/or X-rays or electron-radiation, one of these kinds of radiation being used for irradiating the deposited layer in the spatial defined areas. If the term "lithographic" production of fine structures is used in the context of the present invention, it normally refers to a photolithographic method. The more general term without the part "photo" is, however, deliberately used here, to not exclude an electron beam or any other particle beam, which would not fall under the general term "photolithography", from the possible means for irradiating the radiation sensitive material. For the same reason, it is referred here to irradiating the layer instead of illuminating the layer.

As already mentioned previously, in developing the layer, either its irradiated or its not irradiated spatial areas may be removed.

In the new lithographic method, the layer cannot only be examined for the present of the desired fine structure after it has been developed, but this is already possible earlier, if irradiation of the layer does not only change the state of the material of the layer but also results in a permanent change of state, generally into a destruction, of the luminophore. Due to the strong radiation used in lithographic production of fine structures, such a coinciding destruction of the luminophore will usually occur. Thus, with examining the layer directly after irradiation, it can be checked whether irradiation took really place in the desired spatially defined areas or whether any such areas have been omitted or whether any undesired areas have been irradiated.

If, in examining the layer for the presence of the desired fine structure, the luminescence light emitted by the luminophore is imaged with at least one optical element which is also used in irradiating the deposited layer, this optical element is used twofold, and it is only necessary to adjust it once with regard to the layer. In general, it may be considered to use the whole relevant optics both for irradiating the deposited layer and for examining the layer for the presence of the desired fine structure.

In examining the layer for the presence of the desired fine structure, the luminescence light emitted by the luminophore can advantageously be imaged with an immersion objective. The microscopic examination of the layer on the basis of the luminescence light does not require a difference between the refraction indices between the layer and the adjacent medium.

In the new method, the fine structure of the layer is not imaged directly, i.e. as such; instead the distribution of the luminescence light emitted by the luminophore which is still functioning is detected, which allows for an indirect conclusion with regard to the fine structure. By using an immersion objective in combination with an immersion medium, the refraction index of which is as close as possible to the refraction index of the layer of interest, optimum optical conditions for a high spatial resolution are achieved.

However, it is particularly preferred in the new method, if the immersion medium is not only optimized solely with regard to its refraction index but also with regard to its complete removability from the examined fine structure. To this end, completely volatile liquids, like for example ultra pure water, which do not act as a solvent for any substance included in the layer or a substrate, are particularly suitable. Solid bodies to be placed on the respective layer may also be considered as an immersion medium (known as Solid Immersion Lenses), plus any combinations of liquids and solid bodies.

At present, immersion objectives are already used in the production of lithographic fine structures for irradiating the layer with high spatial resolution. These or similar immersion objectives can also be used in the step of microscopically examining the fine structure in the new method.

The new method does not require locking the layer with the produced fine structure into any high vacuum equipment. Thus, it sets the pre-conditions for microscopically examining any and all produced fine structures at acceptable efforts. The efforts necessary are particularly low, if optical elements are used for the examination of the fine structure, which are also used for irradiating the layer for forming the fine structure. If the main measures for increasing the spatial resolution described here are applied, spatial resolutions in measuring the luminescence light emitted by the luminophore are possible with which periodic line structures of a width of 80 nm and a distance of 40 nm or with an even finer design can be analyzed with luminescence light and optical signals in the visible range.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
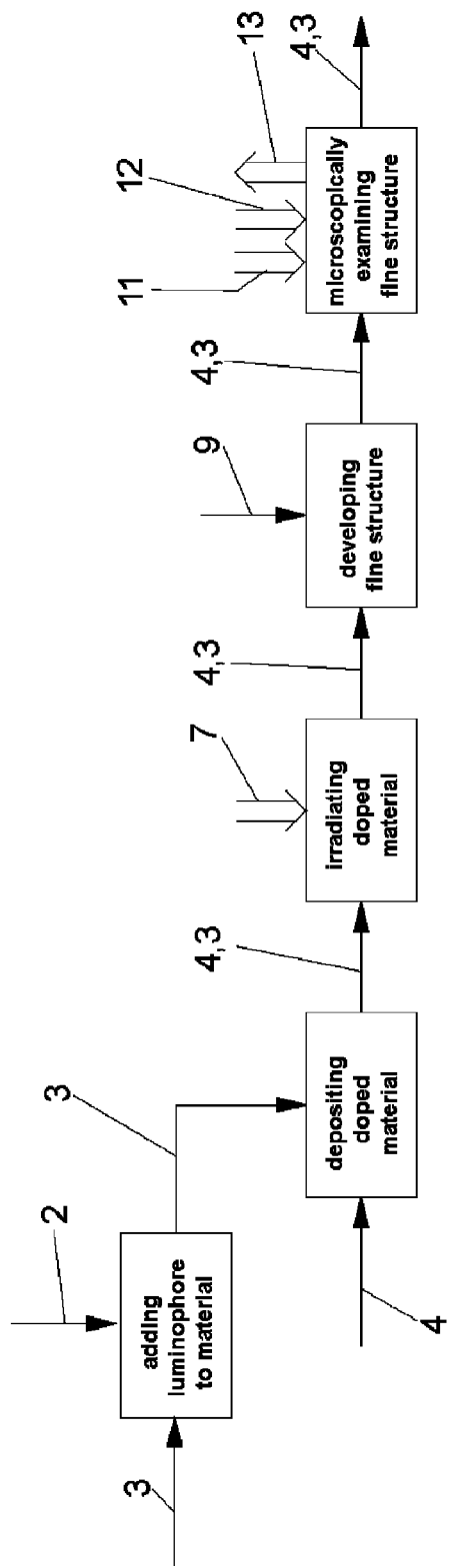
FIG. 1 is a block diagram depicting the steps of the new method in a first embodiment.

Referring now in greater detail to the drawings, the method schematically depicted in FIG. 1 starts with a step 1 of adding a fluorescence dye 2 to a radiation sensitive material 3. The concentration at which the fluorescence dye 2 is added to the material 3 typically is $10^{-7}$ to $10^{-6}$ mol. The material 3 doped with the fluorescence dye 2 is then deposited 5 onto a substrate 4 to form a substrate 4 provided with a layer of the material 3. In a following step of irradiating 6 with a radiation 7, the chemical state of the radiation sensitive material 3 of the layer is basically changed in spatially defined areas by the radiation 7. The parts of the material 3 amended in this way is removed in the following step of developing 8 using a developer 9 so that only the previously not irradiated parts of the material 3 remain on the substrate 4. The fine structure formed by the material 3 remaining on the substrate is examined in a step of fluorescence microscopically examining 10 whether exactly that fine structure is present which was to be formed by irradiation 6 with the radiation 7. For fluorescence microscopically examining 10, the fluorescence dye 2 in the material 3 is excited with an excitation beam of light 11 but everywhere outside measuring points of interest it is de-excited again with a de-exciting beam of light 12, so that fluorescent light 13 which is analyzed in fluorescence microscopically examining 10, always only comes out of a strongly delimited spatial area. At the end of the method according to FIG. 1, there is a substrate 4 on which the material 3 demonstrably forms the desired fine structure defined by the irradiation 6 with the radiation 7.

Figure 2:
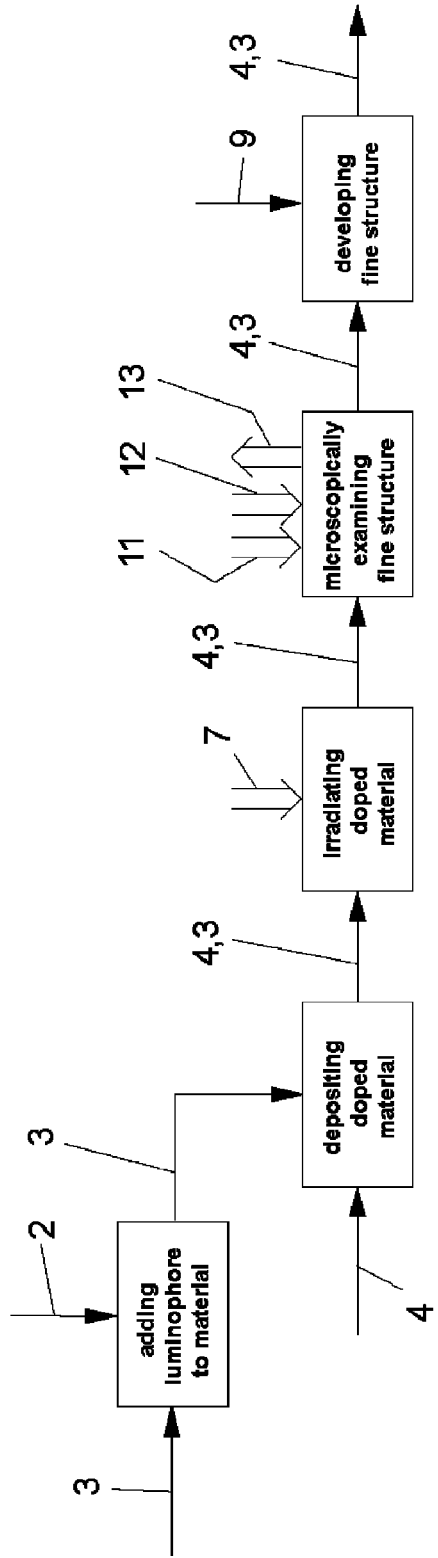
FIG. 2 is a block diagram depicting the steps of the new method in a second embodiment.

The variant of the method depicted in FIG. 2 differs from that one according to FIG. 1 only after the step of irradiating 6. According to FIG. 2, the fine structure is fluorescence microscopically examined 10 directly afterwards, i.e. even prior to developing 8. This variant of the method according to FIG. 2 is based on that the radiation 7 does not only change the material 3 as such but also the added fluorescence dye 2 permanently, so that not only after developing 8, i.e. after removing the irradiated parts of the material 3, the distribution of the still functioning fluorescence dye 2 indicates the fine structure produced by the radiation 7. This fine structure can be examined directly after irradiating 6, and developing 8 can take place afterwards. Thus, only those layers will be developed, in which the desired fine structure has actually been produced by the radiation 7. In addition, if an immersion objective has been used for imaging the radiation 7 into the material 3 of the layer on the substrate 4, the same immersion objective can also be used for imaging the excitation beam of light 11 and the de-excitation beam of light 12 as well as for collecting the fluorescence light 13 from the fluorescence dye 2.

Figure 3:
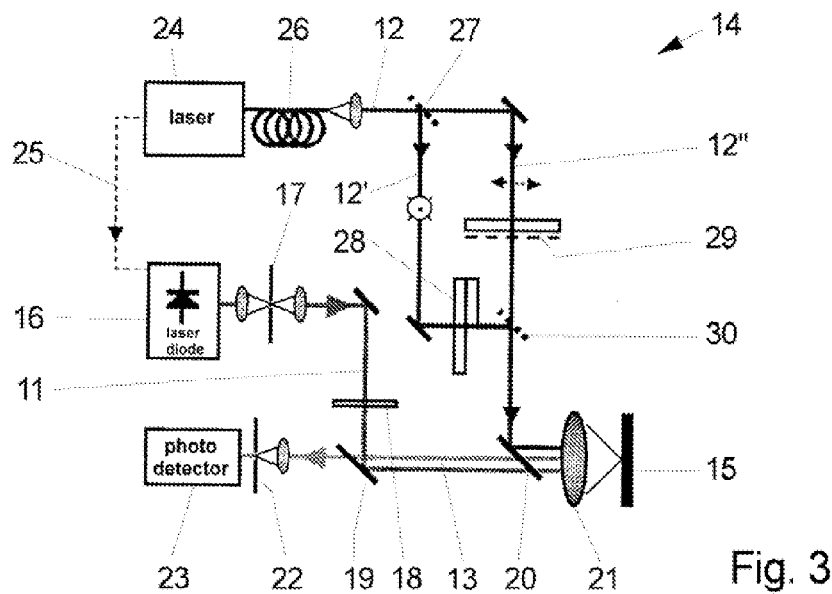
FIG. 3 shows the principle design of a fluorescence microscope used in the method according to FIG. 1 or FIG. 2.

FIG. 3 shows the principle design of a fluorescence microscope, which can be used in the step of examining 10 according to FIGS. 1 and 2. The fluorescence microscope 14 has an excitation light source 16 for exciting the fluorescence dye in the sample 15, which is a pulsed laser diode (PicoQuant GmbH, Germany) emitting the excitation beam of light 11 at a wavelength of 635 nm in 68 ps pulses with a repetition rate of 80 MHz. The excitation beam of light 11 is directed from the excitation light source 16 through a pinhole 17 and then gets through a λ/4-plate which circularly polarizes the excitation beam of light 11. After deflection by dichroitic mirror 19, the excitation beam of light 11 gets through a further dichroitic mirror 20 into an objective 21, and it is focused by the objective 21 into the sample 15. Here, the objective 21 is an oil immersion objective having a numeric aperture of 1.4 (Planapo 1.4 NA, Leica Microsystems, Wetzlar, Germany). The dichroitic mirrors 19 and 20 and further filters which are not depicted here are adjusted to a wavelength of the exciting beam of light 11 of 635 nm and to an emission range of the fluorescence dye in the sample 15 of 650 to 710 nm, these characteristics belonging to the xanthene-fluorescence dye JA 26. Fluorescence light 13 out of the sample is collected by the objective 21 and projected onto a pinhole 22 in front of a photo detector 23. The pinhole 22 is confocally arranged with regard to the pinhole 17 in the optical path of the excitation beam of light 11. The pinhole 22 and the photo detector 23 can be realized by means of a light guide fiber, which guides the light to a counting avalanche photodiode. The core diameter of the light guide fiber may advantageously correspond to the 0.7-fold diameter of the Airy-disc in the image in the focal plane of the objective 21.

This design of a construction of a confocal fluorescence microscope is augmented by the following parts to have an STED fluorescence microscope, the dichroitic mirror 20 already belonging to this augmentation. In an STED microscope, the dimensions of the volume, in which the fluorescence dye is still excited so that it can emit fluorescence light 13, are reduced by depleting the excited state of the fluorescence dye by means of stimulated emission in all areas except of the measuring point of interest. For providing the respective de-excitation light beam 12, the fluorescence microscope 14 comprises a de-excitation light source 24, which is a Ti:sapphire laser with phase coupling in the femto-second-range (Mai Tai, Spectra Physics) emitting the de-excitation light beam 12 at a wavelength of 780 nm and providing a trigger signal 25 for the exciting light source 16. The red-shifted pulses emitted by the de-excitation light source 24 are guided through a single mode fiber of 100 m length to extend their pulse duration to 300 ps. Thus, the pulses of the de-excitation light beam 12 are essentially longer than those of the excitation light beam 11 of 68 ps. In this way, an undesired excitation of the fluorescence dye which is not de-excited afterwards is omitted. The single mode fiber 26 does not affect the polarization of the de-excitation light beam 12, which is afterwards split up by a polarizing beam splitter 27 in two partial beams 12' und 12" having s- and p-polarizations orthogonal to each other. After passing through phase plates 28 and 29, which tune the polarizations of the partial beams 12' and 12" with regard to each other, the partial beams 12' and 12" are superimposed again by a further polarizing beam splitter 30 in such a way that the de-excitation beam of light 12 imaged into the sample 15 by the objective 21 forms an interference pattern having a torus-shaped area having an intensity >0. This interference pattern has a zero point, i.e. an intensity of 0, in the center of the torus-shaped area. In this zero point, the excitation of the fluorescence dye in the sample 15 is not de-excited by means of the de-excitation beam of light 11, whereas everywhere outside of this zero point de-excitation occurs due to the excitation beam of light 12. In this way, the resolution of the fluorescence microscope 14 can be kept below the diffraction limit of the excitation beam of light 11 used for exciting the sample.

Figure 4:
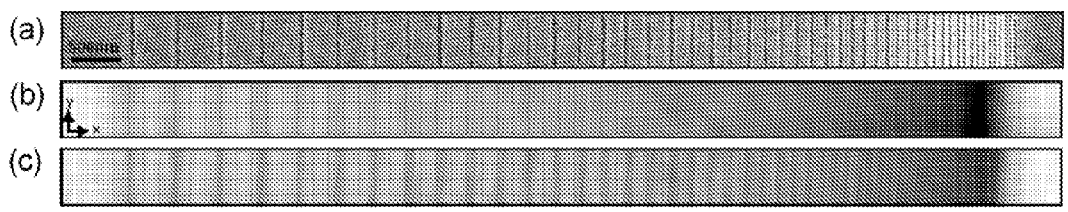
FIG. 4 shows images of a line pattern with decreasing line distance taken by scanning electron microscopy, confocal fluorescence microscopy and STED fluorescence microscopy.

FIG. 4 shows images of a fine structure which has been produced in the following way. Polymethylmethacrylate (PMMA, molecular weight about 450,000, 40 µM) in (2-methoxylethyl)-acetate as the material 3 was doped with the fluorescence dye JA 26 (molecular weight about 500, 100 µM). This doped material 3 was applied to a substrate 4 of silicon at a layer thickness of 40 to 50 nm, and then baked at 110° C. for one hour to remove any solvent residues. Afterwards, an electron beam (5 kV, 0.1 mC/cm) which induced breaking up of the bondings in the PMMA-polymer chain increasing the differential solution of the PMMA was used to write a fine structure into the baked layer. Afterwards, the irradiated layer was developed with a developer solution consisting of a solvent (ethyleneglycolmonoethylether and ethyleneglycolmonobutylether 4:1, 45 s developing time). PMMA which was dissolved out of the layer had a plurality of broken bondings per polymer chain due to the irradiation. The non-linearity of the induced solubility of the PMMA resulted in comparatively sharp edges, which were visible in imaging the achieved PMMA-structure by scanning electron microscopy (see FIG. 4(a)). The fluorescence dye 2, which was added to the PMMA here, was already bleached, i.e. made inactive, by breaking up one bond within the dye molecule. Correspondingly, the areas in which the dye is destroyed after irradiation of the PMMA with the electron beam are less sharply delimited than the edges of the removed or remaining areas of the PMMA itself. Nevertheless, FIG. 4(c), which shows an image of the same structure as in FIG. 4(a) taken by STED-fluorescence microscopy, separately displays the same lines down to a distance as low as 40 nm. In the confocal fluorescence microscopic image according to FIG. 4(b), these lines can only be distinguished at a much higher distance.

Figure 5:
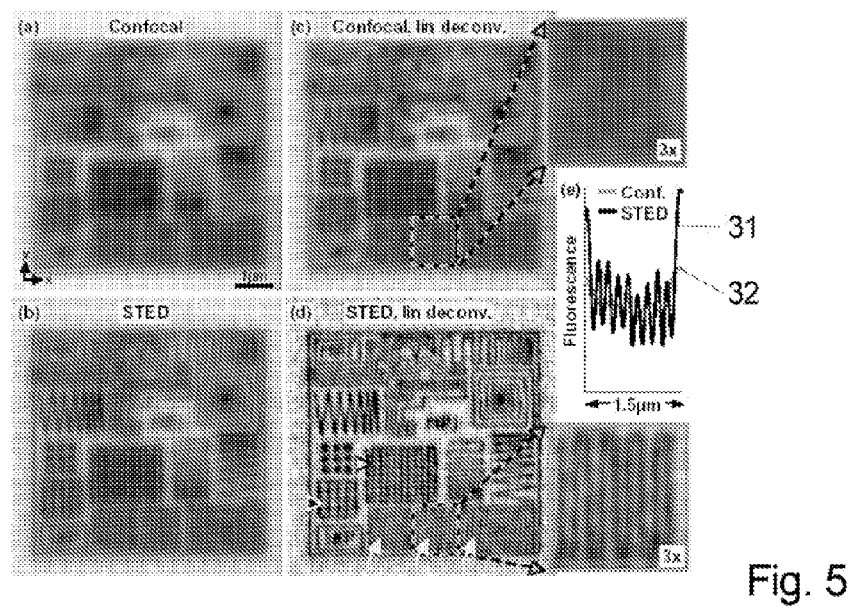
FIG. 5 shows images of various lithographic patterns taken by fluorescence microscopy and STED-fluorescence microscopy.

FIG. 5(a) to (d) shows four different images of the same structures which had been produced according to the description of FIG. 4. FIG. 5(a) is a confocal fluorescence microscopic image; here, the structures are hardly resolved. The picture according to FIG. 4(b) is a STED-fluorescence microscopic picture and already resolves the structures quite good. In FIG. 5(d) the structures are visible very well; this figure represents the picture according to FIG. 5(b) after amplifying the higher spatial frequencies of the picture by means of a numeric Wiener-filter. Here, patterns having a line distance of 80 nm (white arrows) are clearly resolved. A pattern having a line distance of 140 nm (white arrowheads) is even better resolved. A pattern having a line distance of 200 nm (black arrowheads) is very clearly visible. The resolution of one of the patterns having a line distance of 80 nm is particularly visible in the enlarged detail according to FIG. 5(d). FIG. 5(c) is the image according to FIG. 5(a) processed in the same way as FIG. 5(d). Here, the details of the structure of interest are not resolved even in threefold magnification. The differences between the images of FIGS. 5(c) and 5(d) with regard to the enlarged detail are particularly apparent from FIG. 5(e). Here, the intensity variation of the fluorescence light along a horizontal section at half height through the enlarged area is plotted. The spatial profile 31, which belongs to the STED fluorescence microscopic image, clearly shows intensity modulations having the spatial positions of the viewed structure, whereas the spatial profile 32 belonging to the confocal image only indicates the borders of the viewed structure. The intensity modulation of the profile 31 amounts to more than 20%, even if calculated with regard to the maximum signal at the right border of the section. Within the section, the intensity modulation between the minima and the maxima as calculated with regard to the maxima of the fluorescence light amounts to at least 30%.

Many variations and modifications may be made to the preferred embodiments of the invention without departing substantially from the spirit and principles of the invention. All such modifications and variations are intended to be included herein within the scope of the present invention, as defined by the following claims.

We claim:

1. A method of producing spatial fine structures comprising the steps of:
   selecting a luminophore from the group of luminophores displaying two different states, one of the two states being an active state in which luminescence light is obtainable from the luminophore, the other of the two states being an inactive state in which no luminescence light is obtainable from the luminophore, and the luminophore being reversibly, but essentially completely, transferable out the one state into the other state by means of an optical signal;
   adding the luminophore to a material;
   forming a spatial fine structure of the material; and
   fluorescence-microscopically examining whether the desired fine structure is present, the step of fluorescence-microscopically examining comprising the sub-steps of:
      outside measuring points of interest, transferring the luminophore into the other state with the optical signal, the luminophore being essentially completely transferred into the inactive state outside the measuring points, and
      measuring luminescence light only emitted by the luminophore in the active state.

2. The method of claim 1, wherein, in the step of fluorescence-microscopically examining, even lines at a distance of less than 100 nm are resolved.

3. The method of claim 2, wherein, in the sub-step of measuring, an intensity modulation of the luminescence light over a scan across the lines amounts to at least 20% of a maximum intensity of the luminescence light during the scan.

4. The method of claim 1, wherein, in the step of transferring, the luminophore is transferred into the inactive state by stimulated emission depletion.

5. The method of claim 1, wherein, in the step of transferring, the luminophore is transferred into the inactive state by ground state depletion.

6. The method of claim 1, wherein, in the step of adding, the luminophore is added to the material at a concentration between $10^{-8}$ Mol/liter and $10^{-2}$ Mol/liter.

7. The method of claim 6, wherein, in the step of adding, the luminophore is added to the material at a concentration between $10^{-7}$ Mol/liter and $10^{-6}$ Mol/liter.

8. The method of claim 1, comprising the additional step of selecting the material from the group of radiation sensitive materials, and wherein the step of forming comprises the sub-steps of
   depositing a layer of the material onto a substrate,
   irradiating the deposited layer within spatially defined areas, and
   developing the irradiated layer in that parts of the layer are removed and the desired fine structure remains.

9. The method of claim 8, wherein, in the step of selecting, the material is selected from the group of radiation sensitive materials consisting of materials sensitive to x-rays and materials sensitive to electron radiation.

10. The method of claim 8, wherein, in the sub-step of developing, the irradiated areas of the layer are removed.

11. The method of claim 8, wherein, in the sub-step of developing, the not irradiated areas of the layer are removed.

12. The method of claim 8, wherein the step of fluorescence-microscopically examining is carried out prior to the sub-step of developing.

13. The method of claim 8, wherein the step of fluorescence-microscopically examining is carried out after the sub-step of developing.

14. The method of claim 8, wherein, in the sub-step of irradiating, the luminophore is destroyed in the irradiated areas of the layer.

15. The method of claim 8, wherein, in the sub-step of measuring, at least one optical element is used for imaging the luminescence light emitted by the luminophore onto a detector, which optical element is also used in the sub-step of irradiating.

16. The method of claim 1, wherein, in the sub-step of measuring, an immersion objective is used for imaging the luminescence light emitted by the luminophore onto a detector.

17. The method of claim 16, wherein, in the sub-step of measuring, a volatile liquid is used as an immersion liquid in combination with the immersion objective.

18. A method of producing spatial fine structures comprising the steps of:
   selecting a material from the group of radiation sensitive materials;
   selecting a luminophore from the group of luminophores displaying two different states, one of the two states being an active state in which luminescence light is obtainable from the luminophore, the other of the two states being an inactive state in which no luminescence light is obtainable from the luminophore, and the luminophore being reversibly, but essentially completely, transferable out the one state into the other state by means of an optical signal;
   adding the luminophore to the material;
   forming a spatial fine structure of the material, the step of forming comprises the sub-steps of:
      depositing a layer of the material onto a substrate,
      irradiating the deposited layer within spatially defined areas, and
      developing the irradiated layer in that parts of the layer are removed and the desired fine structure remains; and
   fluorescence-microscopically examining whether the desired fine structure is present, the step of fluorescence-microscopically examining by which even lines at a distance of less than 100 nm are resolved comprising the sub-steps of:
      outside measuring points of interest, transferring the luminophore into the other state with the optical signal, the luminophore being essentially completely transferred into the inactive state outside the measuring points, and
      measuring luminescence light only emitted by the luminophore in the active state, an intensity modulation of the luminescence light over a scan across the lines at a distance of less than 100 nm amounting to at least 20% of a maximum intensity of the luminescence light during the scan.

19. The method of claim 18, wherein, in the step of transferring, the luminophore is transferred into the inactive state by stimulated emission depletion.

20. The method of claim 18, wherein, in the step of transferring, the luminophore is transferred into the inactive state by ground state depletion.

21. The method of claim 18, wherein, in the step of adding, the luminophore is added to the material at a concentration between $10^{-8}$ Mol/liter and $10^{-2}$ Mol/liter.

22. The method of claim 21, wherein, in the step of adding, the luminophore is added to the material at a concentration between $10^{-7}$ Mol/liter and $10^{-6}$ Mol/liter.

23. The method of claim 21, wherein, in the step of selecting, the material is selected from the group of radiation sensitive materials consisting of materials sensitive to x-rays and materials sensitive to electron radiation.

24. The method of claim 21, wherein, in the sub-step of developing, the irradiated areas of the layer are removed.

25. The method of claim 21, wherein, in the sub-step of developing, the not irradiated areas of the layer are removed.

26. The method of claim 21, wherein, in the sub-step of irradiating, the luminophore is destroyed in the irradiated areas of the layer, and wherein the step of fluorescence-microscopically examining is carried out prior to the sub-step of developing.

27. The method of claim 21, wherein the step of fluorescence-microscopically examining is carried out after the sub-step of developing.

28. The method of claim 21, wherein, in the sub-step of measuring, at least one optical element is used for imaging the luminescence light emitted by the luminophore onto a detector, which optical element is also used in the sub-step of irradiating.

29. The method of claim 21, wherein, in the sub-step of measuring, an immersion objective is used for imaging the luminescence light emitted by the luminophore onto a detector.

30. The method of claim 29, wherein, in the sub-step of measuring, a volatile liquid is used as an immersion liquid in combination with the immersion objective.

* * * * *